United States Patent
Simopoulos

(10) Patent No.: US 6,942,618 B2
(45) Date of Patent: Sep. 13, 2005

(54) CHANGE DETECTION FOR OPTIMIZED MEDICAL IMAGING

(75) Inventor: Constantine Simopoulos, Menlo Park, CA (US)

(73) Assignee: Siemens Medical Solutions U.S.A., Inc., Malvern, PA (US)

( * ) Notice: Subject to any disclaimer, the term of this patent is extended or adjusted under 35 U.S.C. 154(b) by 182 days.

(21) Appl. No.: 10/465,736

(22) Filed: Jun. 19, 2003

(65) Prior Publication Data

US 2004/0260177 A1 Dec. 23, 2004

(51) Int. Cl.[7] .................................................. A61B 8/00
(52) U.S. Cl. ....................................................... 600/437
(58) Field of Search ................................. 600/437, 438, 600/441–447, 449–472; 73/625, 626; 126/916; 714/48; 382/128, 173, 232, 254–275

(56) References Cited

U.S. PATENT DOCUMENTS

| | | | |
|---|---|---|---|
| 5,579,768 A | 12/1996 | Klesenski | |
| 5,767,922 A | 6/1998 | Zabih et al. | |
| 5,835,163 A | 11/1998 | Liou et al. | |
| 5,844,613 A | 12/1998 | Chaddha | |
| 5,993,392 A | 11/1999 | Roundhill et al. | |
| 6,095,976 A | * 8/2000 | Nachtomy et al. | 600/443 |
| 6,102,859 A | * 8/2000 | Mo | 600/443 |
| 6,398,732 B1 | 6/2002 | Brock-Fisher et al. | |
| 6,398,733 B1 | 6/2002 | Simopoulos et al. | |
| 6,400,902 B1 | 6/2002 | Usui | |
| 6,476,861 B1 | 11/2002 | Min | |
| 6,491,636 B2 | 12/2002 | Chenal et al. | |
| 6,692,442 B2 | * 2/2004 | Brock-Fisher et al. | 600/458 |
| 2002/0108078 A1 | * 8/2002 | Wong et al. | 714/48 |

* cited by examiner

Primary Examiner—Ali Imam

(57) ABSTRACT

Medical image processing is adaptively optimized in response to selective types of changes or motion. Adaptive optimization is applied in response to limited types of motion or at a controlled time. For example, one type of change, such as change due to heart motion or breathing motion, is distinguished from a different type of change, such as change due to repositioning of an imaging plane within a patient. Imaging parameters are adaptively optimized in response to changes of one type independent of or with minimized contribution from changes of the different type. For example, change due to repositioning of the image plane is detected while accounting for heart motion or breathing motion. Imaging parameters are adaptively optimized once the change due to anatomical motion is removed or accounted for and after detecting a change in an imaging plane position. Any of various adaptive optimizations may be responsive to the identification of one type of change from another type of change.

20 Claims, 3 Drawing Sheets

CHANGE DETECTION FOR OPTIMIZED MEDICAL IMAGING

BACKGROUND

The present invention relates to medical imaging, and in particular to systems that set one or more image processing parameters.

In ultrasound medical imaging, various imaging parameters are set for acquiring and processing image data. For example, relative delays and apodization for transmit and receive beamforming, depth dependent and overall gains, an amount of persistence or other filtering, weightings, types of filters, spatially compounding variables, dynamic range or other image processing parameters are set. For example, a B-mode signal is adjusted for gain and dynamic range before being mapped to a range of gray levels or colors for display. The dynamic range can conveniently be set by the user by means of a display dynamic range control that is independent of range in azimuth position in the image. The gain can be varied by the user using a depth or time gain compensation control along with a master gain or B-mode gain control. The depth or time gain control may vary in range (axial dimension) while a master gain is independent of both range and lateral (azimuthal) position. As another example, a focal point or depth of imaging is selected for determining beamforming parameters. As yet another example, a type of imaging is selected that uses spatial and/or persistence compounding.

In addition or as an alternative to user selection of the various imaging parameters or user selection of a setup associated with groups of imaging parameters, the imaging parameters may be set adaptively as a function of ultrasound data. For example, U.S. Pat. No. 6,398,733, the disclosure of which is incorporated herein by reference, discloses adaptively determining one or more of gain, dynamic range and post-processing maps in response to ultrasound data. Amplitudes associated with soft tissue are determined and a gain or dynamic range is set in response to the amplitudes. Ultrasound data acquired without transmission of energy or selected as representing noise is used to adaptively determine gain or dynamic range.

The other imaging processing parameters discussed above may also be adaptively varied. For example, focusing delays or apodization values are adaptively determined as a function of ultrasound data to provide for aberration correction. As another example, a filtering parameter, such as a persistence or spatial compounding parameter, is adaptively varied as a function of ultrasound data, such as to avoid blurring. However, random or statistical fluctuations in the data may cause undesired optimization, resulting in flickering through an entire image or within local regions of an image.

To avoid undesired automatic optimization, the adaptive optimization is only initiated in response to a user input. For example, the user selects an automatic gain function, and the system adaptively determines a gain at that given instance in time for application to subsequent data until the user reselects the automatic gain optimization. As another example, the user changes one imaging processing parameter, and the system then automatically optimizes other imaging parameters. However, manually initiating adaptive optimization of imaging parameters slows down work flow. The user is required to make quick and accurate judgments during real time imaging as to when to apply the optimization, often resulting in images not being optimal.

U.S. Pat. No. 6,579,238 (U.S. application Ser. No. 09/791,405, filed Feb. 23, 2001), the disclosure of which is incorporated herein by reference, discloses initiating the adaptive adjustment of gain or dynamic range automatically at intervals. However, initiation of adaptive optimization of imaging parameters at regular intervals may be distracting or annoying to the user. Depending on how often the optimization is applied, a frame rate reduction or unacceptable delays between optimizations may result. Detecting large changes in the input signal, such as a large change in the sum of input signals for a frame of data or a region of a frame of data, is also disclosed for initiating adaptive optimization. Detection of large motion signals based on frame correlation may also be used to initiate adaptive adjustment of gain or dynamic range. Initiating adaptive optimization of imaging parameters based on large changes or motion detection may be susceptible to noise, flash artifact, changes in the anatomy or region of the anatomy being imaged. With too sensitive of detection of change or motion, change due to heart motion may automatically initiate adaptation, resulting in variance between images due to imaging parameters rather than anatomy differences.

In video cameras, motion due to object motion as opposed to panning and shaking of the video camera may be separately identified for different processing of the video information. For example, see U.S. Pat. No. 5,767,922 Zabih, et al "Apparatus and process for detecting scene breaks in a sequence of video frames", U.S. Pat. No. 5,835,163 Liou, et al "Apparatus for detecting a cut in video", and U.S. Pat. No. 5,844,613 Chadda, "Global motion estimator for motion video signal encoding". These patents attempt to separate frame changes due camera panning, motion of objects in the scene and changes due to different video segments filmed at different times. The techniques are computationally very demanding.

BRIEF SUMMARY

The present invention is defined by the following claims, and nothing in this section should be taken as a limitation on those claims. By way of introduction, the preferred embodiments described below include methods and systems for automatically altering medical image processing. Adaptive optimization is applied in response to limited types of motion or at a controlled time. For example, one type of change, such as change due to heart motion or breathing motion, is distinguished from a different type of change, such as change due to repositioning of an imaging plane within a patient. Imaging parameters are adaptively optimized in response to changes of one type independent of or with minimized contribution from changes of the different type. For example, change due to repositioning of the image plane is detected while accounting for heart motion or breathing motion. Imaging parameters are adaptively optimized once the change due to anatomical motion is removed or accounted for and after detecting a change in an imaging plane position. Any of various adaptive optimizations may be responsive to the identification of one type of change from another type of change.

In a first aspect, a method for automatically altering medical image processing is provided. A type of change is automatically identified from frames of data for medical imaging. Image processing is optimized in response to a first type of change differently than to a second type of change.

In a second aspect, an ultrasound medical imaging method for initiating calculation of gain is provided. Change due to the repositioning of an imaging plane is determined based on a calculation from ultrasound data. Change due to one of heart motion, breathing motion and combinations thereof is accounted for in the determination of the change due to the repositioning of the image plane. One of gain, dynamic range and combinations thereof are set adaptively by calculation from ultrasound data. The setting is initiated as a function of the determination of the change due to the repositioning of the image plane.

In a third aspect, a system for automatically altering medical image processing is provided. A control processor is operable to automatically identify a type of change from frames of data for medical imaging and operable to initiate optimized image processing in response to a first type of change differently than a second type of change. A processor is responsive to initiation from the control processor to begin optimization of the image processing.

Further aspects and advantages of the invention are discussed below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automation of an ultrasound or other medical imaging system is enhanced by accounting for different types of motion. Automatic updates or optimization of imaging parameters, such as gain or quantifications, are more robust by detecting change in data due to one type of change and not another type of change. For example, some measure of image change is used to identify whether the change is due to transducer movement as opposed to heart and breathing motion. Features of the change are extracted which characterize one type of motion as opposed to another type of motion, such as removing changes due to the quasi-periodic nature of cardiac and breathing motion to identify change due to more random acts, such as transducer movement.

Figure 1:
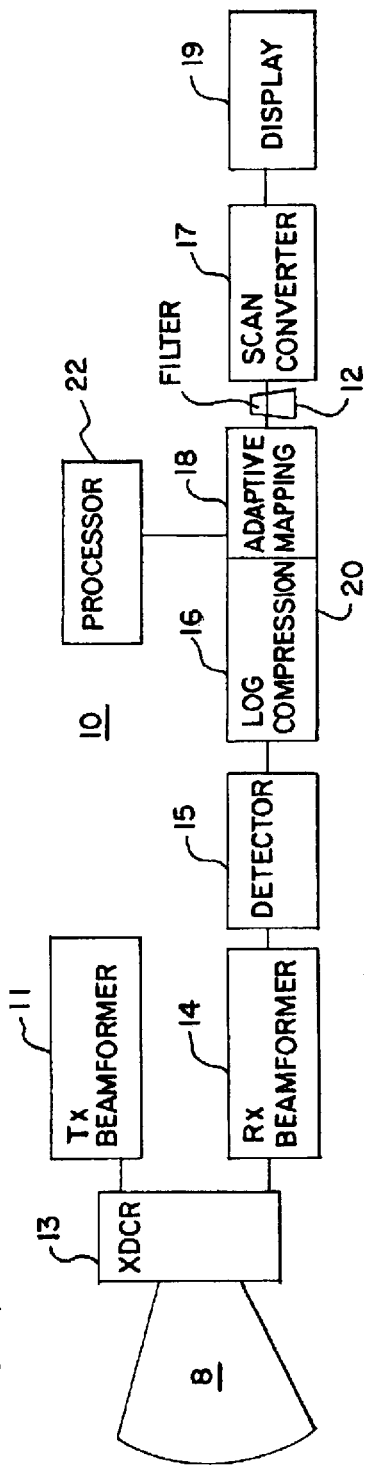
FIG. 1 is a block diagram of a medical diagnostic ultrasound system of one embodiment.

FIG. 1 shows a medical diagnostic ultrasound system for automatically altering medical image processing. In alternative embodiments, the system 10 comprises a different type of medical imaging system, such as a magnetic resonance, computed tomography, x-ray or other imaging system. As shown in FIG. 1, a transmit beamformer 11 applies transmit waveforms via a transmit/receive switch to a transducer array 13. The transducer array 13 produces ultrasonic pulses in response to the transmit waveforms, which pulses are directed into a body to be imaged in an imaging region 8, such as a plane or volume or line. Returning echoes from the body impinge upon the transducer array 13 which converts these echoes into receive signals that are transmitted via the transmit/receive switch to a receive beamformer 14. The receive beamformer 14 applies appropriate delays and phase shits to cause the receive signals from selected locations within the body to add coherently. These beamformed signals are applied to an amplitude detector 15 and a back-end processor 20 that includes a log compression device 16 before being applied to a scan converter 17. The back end processor 20 includes an adaptive multi-dimensional back end mapping stage 18 in one embodiment. Some example adaptive mapping stages 18 are disclosed in U.S. Pat. Nos. 6,398,733 and 6,579,238 (U.S. application Ser. No. 09/791,405), the disclosures of which are incorporated herein by reference. A filter 12 performs any of one-dimensional, two-dimensional, three-dimensional filtering. For example, the filter 12 implements either spatial compounding and/or persistence using an infinite or finite impulse response. The scan converter 17 generates display values on a grid appropriate for a display 19.

All of the elements 11 through 20 can take any suitable form, and are not limited to any particular implementation. For example, the transmit and receive beamformers 11, 14 can be constructed as analog or digital devices, and any suitable transducer array 13 can be used, including a single element, one-dimensional or multi-dimensional transducer array. Also, the system 10 may include additional elements in the signal path between the transducer array 13 and the display 19, and selected ones of the illustrated elements may be deleted or the order of some of the elements may be switched. For example, the order of the back end processor 20 and the scan converter 17 may be altered. As another example, the filter 12 is positioned immediately after the receive beamformer 14, transducer 13, detector is a scan converter 17.

Analog or digital circuitry used for one, all or a part of any of the components 11 through 20 or additional or different components may include an image processing processor for optimizing image processing in response to a control processor 22. For example, the transmit and/or receive beamformers 11, 14 include image processing processors for setting beamforming characteristics, such as phasing, delays and apodization. As another example, the receive beamformer 14 includes a filter for selecting a frequency of interest from the received data. As yet another example, the back end processor 20 includes an image processing processor for determining a system gain, a depth or time gain, dynamic range and/or mapping function. As yet another example, the filter 12 includes persistence and/or spatial compound filter processing. As yet another example, the processor 22 or another processor within the system acts as an image processing processor to quantify or calculate information from frames of data or images, such as detecting an organ boundary, calculating an area or volume or calculating another quantifiable feature. Other image processing and associated image processing processors within the system 10 or another medical imaging system now known or later developed may be used for implementing any of various image processing, including image enhancement and quantification functions.

The image processing processor optimizes the image processing, such as changing the filtering parameters, setting quantification controls, thresholds, algorithms or otherwise selects a variable or function in response to an initiation signal from the control processor 22. The image processing is performed as a function of precalculated, manually set or adaptive functions. For adaptive functions, an image processing parameter is a function of the data obtained by the system 10 from the patient. For example, a gain is calculated as a function of received ultrasound signals associated with soft tissue. Any now known or later developed adaptive image processing may be used. Alternatively, manually set or precalculated optional image processing parameters may be used without automatic calculation from acquired data representing the patient.

The control processor 22 is a digital signal processor, general processor, application-specific integrated circuit, analog device, digital logic or combinations thereof for controlling one or more of the image processing processors of the system 10. In one embodiment, the image processing processor and the control processor 22 are a same device, but different devices may be used. In one embodiment, the control processor 22 is separate from other components of the system 10, but part or all of the control processor 22 may be included with one or more of the components of the system 10. In one alternative embodiment, an R-wave, ECG or breathing monitor connects with the control processor 22 or other component of the system 10.

The control processor 22 automatically identifies a type of change represented from a plurality of frames of data for medical imaging. The control processor 22 initiates optimization of image processing in response to a first type of change differently than a second type of change. For example, the control processor 22 identifies change due to transducer motion from change due to more cyclical motion. Image processing parameters or processing in general is kept constant or changes minimally due to cyclical motion. Change due to repositioning of a transducer is identified and the image processing is optimized in response to the new region being scanned. For example, adaptive gain, adaptive persistence, adaptive spatial compounding, adaptive beamforming and/or other adaptive image processing is initiated once a transducer has been moved and is in a stable position. As a result, optimization due to cyclical motion and the associated cyclical variation in imaging is avoided while adaptive processes are optimized to any given scanning region of the patient. Gain, mapping, dynamic range, beamforming or quantification are adaptively altered after transducer motion is stable but in response to identification of change due to transducer motion. The differences in the tissue or region imaged may affect the optimized image processing so are adaptively changed once a transducer is positioned. The initiation of the optimization of image processing is performed without manual intervention at the time of the initiation, but may include manual intervention.

Figure 2:
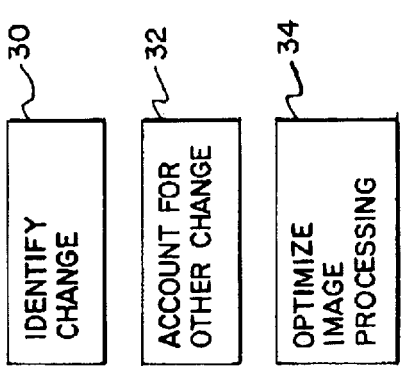
FIG. 2 is a flowchart diagram of one embodiment for adaptive image processing in response to different types of change.

FIG. 2 shows a flowchart of a method for automatically altering medical image processing. Additional, different or fewer acts may be provided. In act 30, a change is automatically identified from frames of data for medical imaging. In one embodiment, one type of change is sensed without use of the received imaging data, such as by using an R-wave, ECG or breathing monitor. The change due to the monitored cycles is then accounted for by subtraction, disabling initiation of optimization or other function. For example, change detected during minimal motion of the heart is likely change due to transducer movement and change detected during active portions of the heart cycle is likely to be due to motion of the heart.

In another embodiment, the changes are detected from the received data, such as from ultrasound data. The change is determined or calculated from received data in any of various formats, such as a set of frames representing sequential scans of a region of a patient. Different types of change are identified as a function of time, such as cyclical changes associated with heart or breathing cycles, and more random or less cyclical changes, such as due to transducer motion or differences in an imaging plane or region.

In order to detect changes in a sequence of images or frames of data, each frame of data is compared with a reference frame of data. A single reference frame for comparison with all other frames of data may be used, but an immediately preceding or other frame of data may be used as the reference frame of data in other embodiments. In one embodiment, the reference image is a combination of a plurality of images, such as previous images combined by infinite impulse response filtering. To perform the comparison, a change parameter is calculated as a function of time. For example, each frame of data is divided into a plurality of regions, such as 10×10 regions. Other decimation to simplify computation may be used. Alternatively, an entire image is used. Each region contains one or more pixels. An average intensity or other value for each region is calculated. The average intensities for each corresponding region between a current frame of data and a reference frame of data are calculated. Any of various change parameters may be used, such as the sum of squares of the differences, the sum of absolute differences, a correlation or other value. In one embodiment, the regions are correlated as opposed to comparing an average or other representative value of a region.

The average intensities, change parameter or other value from each region are averaged to determine a value for each frame of data or image. The resulting difference value is compared to a threshold, such as a threshold determined through experimentation as a function of the type of imaging system and application. If the change parameter exceeds the threshold, then a change is identified. Alternatively, if a sum of squares of the differences for a plurality, all or other subset of the regions in the frames of data exceeds the threshold, then a change is identified.

Figure 3:
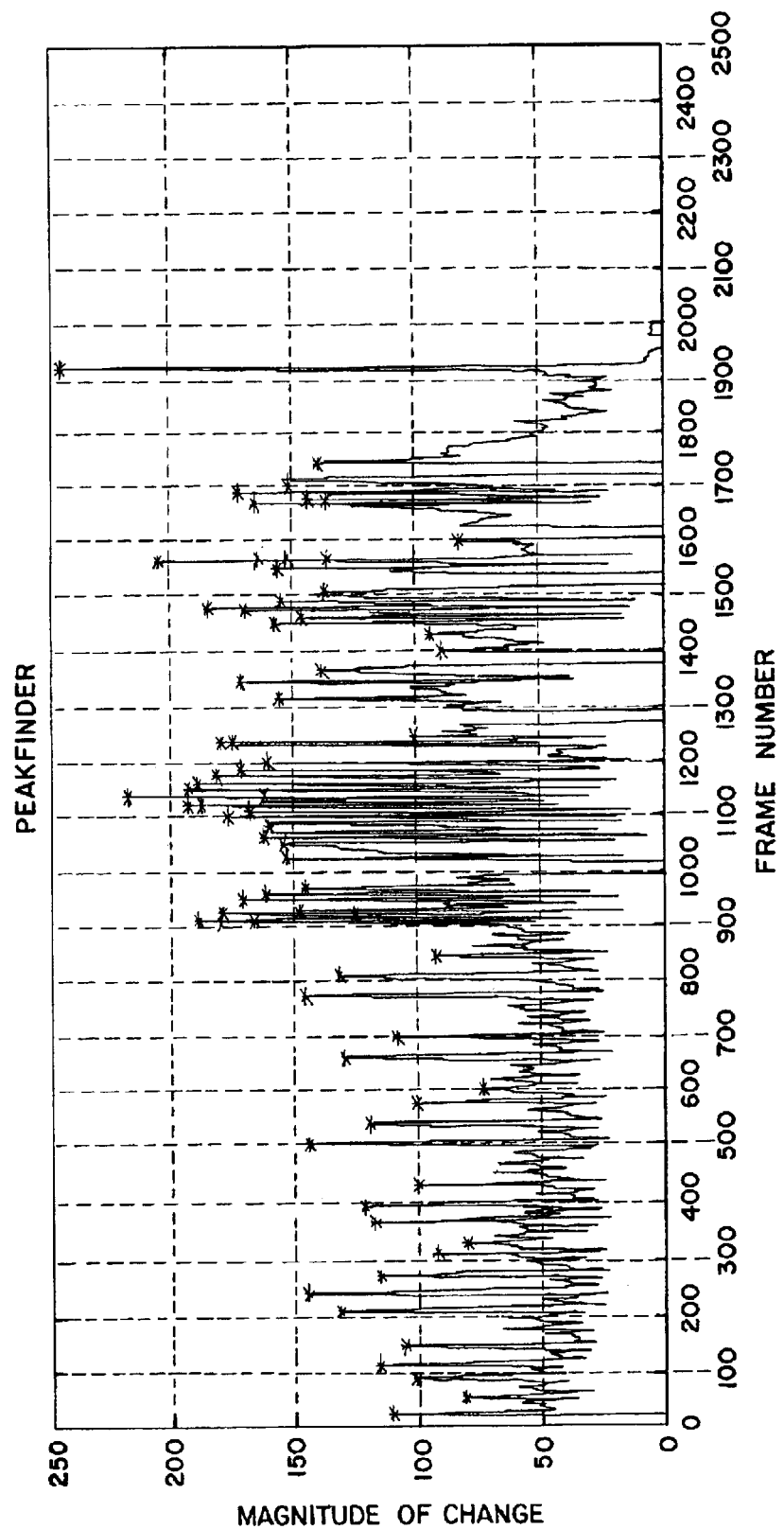
FIG. 3 is a graph of magnitude of change as a function of the frame number or time in one embodiment.

The change parameter is calculated for a plurality of frames of data, resulting in calculation of the change parameter as a function of time. For example, FIG. 3 shows the average sum of square differences based on average intensities for 10×10 regions plotted as a function of the frames of data or time. Comparing values from one frame of data with values from another frame of data indicates the change between the frames of data.

As shown in FIG. 3, regular cyclical changes occur, such as associated with imaging the heart. The portion of the graph in FIG. 3 from the origin of the ordinate axis to about 1000 frames consists of changes due to heart motion. The rest of the data to the end of the ordinate axis is due to transducer translations or a combination of translation and heart motion. Due to natural heart variations, the magnitude of the change, peak width or other variation may not be identical during each repetition of the cycle. A low-pass filter or other filter may be applied to the change parameter to remove low magnitude, high frequency variation. A high pass filter or other filtering may be used to remove other undesired motion.

To identify one type of motion or change from another type of motion or change using the received data, motion or change due to one of the types of motion, such as heart, breathing and motions that are combinations thereof is accounted for in the determination of or identification of change in act 32. In one embodiment, change due to movement of the imaging plane or scan region relative to the patient is identified so that changes due to repositioning of an imaging region are determined. Depending on the image processing parameter to be initiated or altered, one type of change is distinguished from another type of change. For example, a first type of change is identified after accounting for changes due to a second type of change. By either sensing, modeling or calculating change or motion due to heart or respiration and subtracting or otherwise accounting for its effects in overall image changes, changes due to image region translations are more accurately detected. For example in cardiology, a change in the image plane or view rather than change due to heart wall motion or valve motion is identified for re-optimization of adaptive image processing parameters. For example, peaks of the change parameter as shown in FIG. 3 due to cyclical motion are subtracted, minimized or otherwise reduced so that other types of change remain in the plot of FIG. 3.

A model or predicted motion for one type of motion is obtained, such as by modeling cyclical motion while keeping the transducer still. In one embodiment for real time automatic adaptive optimization, the cyclical changes are modeled as a function of the past comparisons or change parameters. The modeled change parameter is subtracted from the current change parameter to account for changes due to cyclical motion. A change value for a current image or frame of data is predicted based on a model conditioned on all or some of the previous change parameters or frames of data. Any of various models may be used, such as an auto regressive, auto regressive moving average, state space model, Kalman filters or other now known or later developed model algorithms. In the embodiment discussed above, the change parameter as a function of time is modeled, but changes in pixels or groups of pixels may alternatively be modeled.

In another embodiment, the prediction is implemented based on a peak detector or finder. The peak detection algorithm may be any of now known or later developed algorithms. In one embodiment, a maximum magnitude of change over a given time period in a moving window is determined. By accounting for the suddenness of the change or the amount of change above a base line, peaks associated with relative small magnitudes or undesired changes may avoid being labeled. In one embodiment, the peak detection algorithm identifies locations in the graph of the change parameter where a monotonic increase is followed by a monotonic decrease. The ascension and following descension are both compared to a threshold or a set of thresholds in order for the highest magnitude to be identified as a peak. The peaks shown in FIG. 3 identified by the peak finding algorithm discussed above are labeled with stars.

The identified peaks and peak intervals provide a prediction of a current change due to cyclical motion. Using correlation or other processes, one or more cycles associated with the change parameter are determined. An average of the peaks over a few cycles provides an accurate prediction of a current change parameter as a function of frame or time. By averaging the magnitude and interval of the peaks, the accuracy of the prediction may be improved.

A current actual change parameter is then compared to the predicted change parameter. If the two change parameters differ beyond some error margin, then a change due to image plane movement is identified while accounting for changes due to cyclical motion. To determine the accuracy of the prediction, a standard deviation of the time intervals of the detected peaks is performed. If the standard deviation is higher than a particular threshold, the prediction may be inaccurate.

Figure 4:
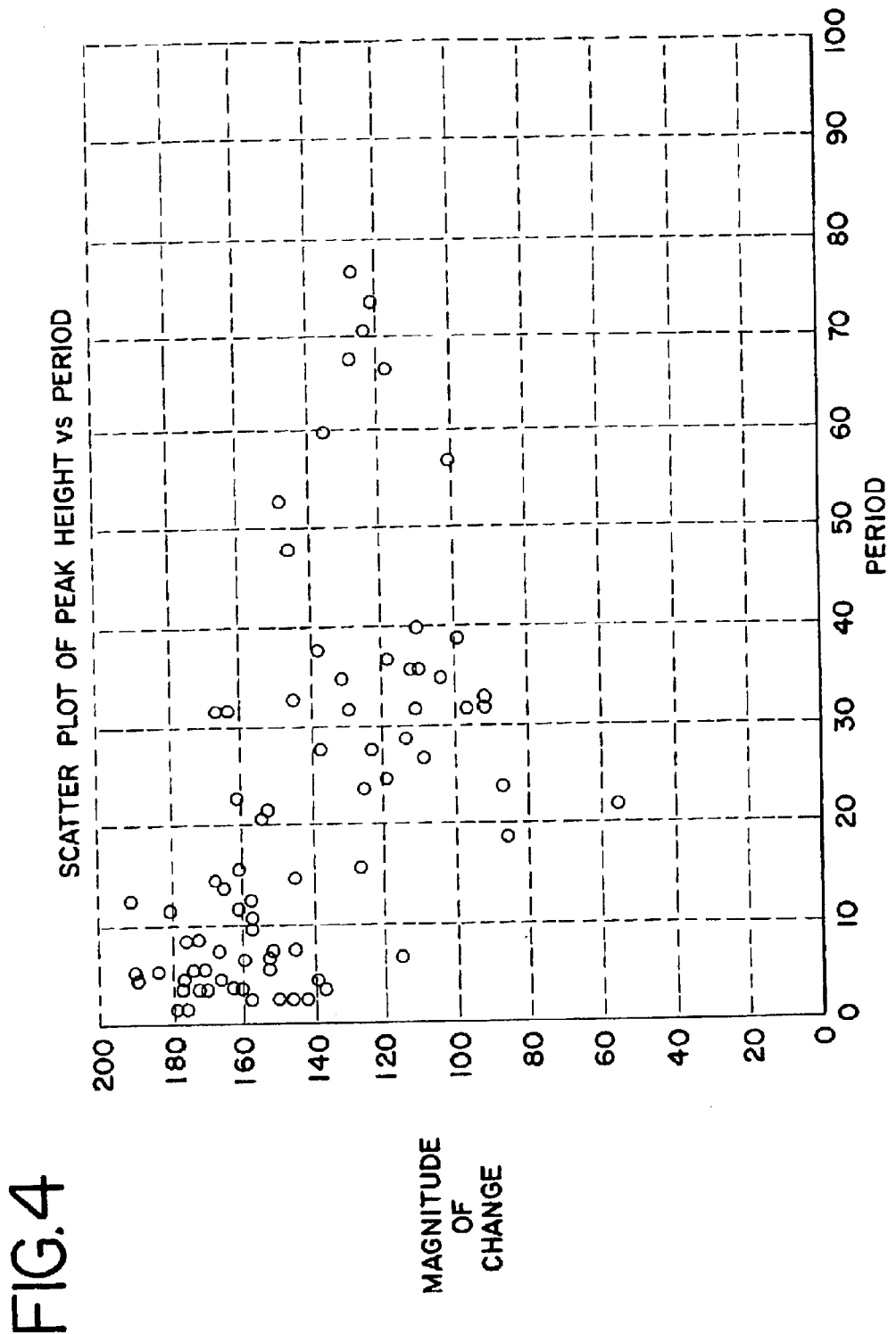
FIG. 4 is a scatter plot of peak height versus period for the peaks of FIG. 3.

Alternatively, the height of the peak is correlated with the time interval that elapsed since the previous peak as shown in FIG. 4. Change parameter peaks due to heart motion or other cyclical motion will tend to cluster around a particular region of periods and magnitudes. Peaks due to other changes, such as when the transducer is being moved, tend to have short intervals and larger magnitude. By identifying regions of a scatter plot shown in FIG. 4 associated with cyclical motion or expected cyclical motion as opposed to regions associated with other types of change, a change for a current frame of data is compared to a period and magnitude thresholds to identify whether the change value is associated with the expected cyclical motion or another change.

In one embodiment, the scatter plot is adaptive to the ultrasound imaging application, such as applying an algorithm to determine when to adjust the regions. For example, small changes in comparison to previously identified cyclical peaks are identified as change due to cyclical motion. Large changes with an interval within a range of the cyclical motion are identified as cyclical motion, but large changes outside the interval range are identified as other motion. In alternative embodiments, the regions are identified based on experimentation and programmed into the system 10.

By comparing each frame of data to a reference frame of data and identifying peaks over a time period, an accurate prediction of an expected change parameter for a subsequent frame of data is developed. The expected or predicted changes, such as due to the cyclical motion, is based on the change parameter or other image over a time period, such as all previous acquisition time, the previous 10 to 20 seconds or other time period. In one embodiment, the user is instructed to hold a transducer as still as possible for a 10 second time period or more to establish a base line for predicting motion due to cyclical changes. Any of various time periods may be used. The period of the heart cycle or other cyclical motion is calculated by counting a number of frames or time between abrupt changes or peaks.

Where an ECG or other sensor indicates a cycle, the update or initiation period of the prediction algorithm may be less, such as associated with only one heart cycle, less than 10 seconds or less than another time period. Less time is used to identify the cycle due to the sensor input. As a result, the prediction is initially based on less data but more determinative time period information. In an alternative embodiment, the ECG or breathing monitor input is used to predict the expected motion directly, such as through an experimentally determined algorithm, and the change is detected by a comparison between the sensor based expected motion and the currently calculated motion or change.

To identify the type of change or change or motion other than cyclical changes, the cyclical change or predicted change is subtracted from, removed or minimized from the current change. For example, the sum of the squares of the differences between a current frame of data and a reference frame of data is compared to an expected change. The difference between the two is compared to a threshold. Alternatively, other functions of the predicted and current change parameter are used to identify a change in addition to the predicted change. In one embodiment, the peak finder is applied to the current magnitude without the descension requirement. If the current magnitude is identified as a peak, the magnitude of the peak and the time since the last peak are compared with an expected peak magnitude and expected time since the last peak. For example, the current peak magnitude and time since the last peak are compared to thresholds to identify a region shown in FIG. 4 indicating change due to a cyclical motion or expected change or change due to other factors. Based on the comparison of the current peak magnitude and the time since the last peak with the thresholds, a change or motion other than the cyclical changes identified.

In FIG. 4, data is clustered in three regions. A first region where the change time intervals are short, below 20 frame periods and magnitude is large, larger than 100 in arbitrary units. This region corresponds to changes due to transducer displacement. The second region is where the change time intervals are between 20 and 40 frame periods and the magnitude above 60 and below 160. This region corresponds to changes due to heart motion. As far as the magnitude of change is concerned, there is some overlap between the two regions. If the time interval between changes is used as an additional discriminating factor, the identification of changes due to transducer displacement becomes more robust. The third region with time intervals between changes from about 50 to 80 and same magnitude change as the second region is again due to heart motion. The change interval is roughly twice the change time interval of the previous region, so for change identification purposes, the second and third region can be considered as one region. Different algorithms or region divisions may account for all or some of the peaks. Division between two or more types of motion may be based on the period alone, the magnitude alone or combinations thereof in any of various possible patterns.

Once a change other than a cyclical change has been identified or detected, the model or algorithm for predicting the change parameter is altered, stopped or maintained. In one embodiment, the change parameter is monitored to identify a time or frame of data associated with a low magnitude of change regardless of any expected cyclical motion. Since the imaging plane may be moved, the cyclical motion may differ in magnitude and period such that cyclical motion is no longer accurate for new positions. Alternatively, predicted motion is accounted for regardless of other changes. Once the motion or change has a lower magnitude indicating no or minimal change, the model or prediction algorithm is updated again with data from the current imaging plane or region. Where a time period is used to establish the predicted parameters, a higher threshold or disabling of the change detection may be implemented for an update interval, such as 10 seconds or so. Alternatively, the thresholds are maintained for a lesser, greater or no update period.

In act 34, image processing is optimized in response to a first type of change differently than a second type of change. For example, optimization or setting of an image processing parameter is initiated in response to change or motion other than cyclical change. As yet another example, change due to transducer motion or imaging plane differences results in automatic optimization of image processing while avoiding the initiation of automatic optimizing in response to heart and/or breathing cycle changes. This robust change detection may reduce false alarms and allow continuous examination of the heart or other cyclically changing organs without triggering undesirable optimization until the transducer is shifted in position.

The setting of an image processing parameter or setting of image processing quantification is initiated as a function of the determination of change. In one embodiment, the setting is automatic based on input from just the received imaging data or frames of data, from response to manual user input or combinations thereof. For example, a change other than cyclical motion change is identified and highlighted to a user. In response to user feedback or without user feedback, image processing is adjusted or altered. In one embodiment, optimization is initiated after the change associated with a particular type of change is stable. For example, a change due to transducer movement is identified and the optimization is not initiated until the change is stable, indicating a lack of change in the position of the imaging plane or region.

In alternative embodiments, detection of the beginning of a change is used to initiate optimization, detection of one type of change as opposed to a different type of change is used to reduce or stop ongoing or continuous optimization, different image processing parameters or quantifications are initiated or ceased in response to different types of changes, cyclical changes result in initiation of image optimization and changes due to transducer motion are accounted for or combinations thereof.

Any of various image processing may be initiated, altered, or ceased in response to the identified change. In one embodiment, an image processing parameter is adaptively optimized as a function of data from one or more frames of data used for identifying the change. In alternative embodiments, adaptive optimization is based on data other than frames of data used for identifying the change.

Any of the adaptive image processing parameters discussed above may be used, such as one or more of gain value, persistence parameters, spatial compounding parameters, beamforming parameters, quantification parameters or other variables selected or calculated as a function of received data representing a region of the patient. For example, adaptive calculation of the gain is initiated in response to movement or a cessation in movement of the imaging region while avoiding the initiation in response to cyclical changes due to the heart of the patient in cardiac imaging. Dynamic range, mapping functions and other imaging parameters may be calculated from the data, such as ultrasound data. For example, any one or more of the adaptive processes taught in U.S. Pat. Nos. 6,398,733 or 6,579,238 (U.S. application Ser. No. 09/791,405). For example, a gain is set adaptively as a function of tissue signals identified from the ultrasound data. Signals having a particular characteristic, such as an amplitude within a range around an average amplitude, mean amplitude or other characteristic identifying the signals as tissue signals are used to calculate a desired gain. As another example, the dynamic range is set adaptively as a function of noise signals from the ultrasound data. One or more frames of data are acquired as noise signals in response to no transmission of ultrasound energy. The dynamic range is selected such that a majority, all or other subset of the noise signals are below the dynamic range. As yet another example, a mapping function is adaptively selected as a function of ultrasound data, such as selecting a mapping function in response to both tissue signal information and noise signals. Depending on the separation of various signals amplitude or other characteristics of the signals, a desired mapping function is selected.

In other embodiments, any of temporal, spatial, frequency of interest, frequency band of interest, or other filter characteristics are adaptively set. Alternatively, any of the image processing parameters discussed herein are optimized by selecting previously stored or predefined values based on a current characteristic or application. In yet other additional or alternative embodiments, a quantification function, variable or algorithm is altered in response to a detected type of change. Alternatively, a quantification is initiated or a value recalculated in response to a detected type of change. Other image processes may be altered in response to detecting the type of change, providing a more automated diagnosis assistance.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for automatically altering medical image processing, the method comprising:
   (a) automatically identifying a type of change from frames of data for medical imaging; and
   (b) optimizing image processing in response to a first type of change differently than to a second type of change;
   wherein (b) comprises automatically optimizing image processing in response to the first type of change being at least one of transducer motion and imaging plane differences while avoiding initiation of optimization in response to the second type of change being at least one of heart and breathing cycle changes.

2. The method of claim 1 wherein (a) comprises identifying change between frames of data associated with at least one of heart and breathing cycles.

3. The method of claim 1 wherein (a) comprises identifying change between frames of data associated with at least one of transducer motion and imaging plane differences.

4. The method of claim 1 wherein (b) comprises adaptively optimizing at least one medical image processing parameter as a function of data from at least one of the frames of data.

5. The method of claim 4 wherein (b) comprises adaptively altering the at least one medical image processing parameter where the at least one medical image processing parameter comprises one of: a gain value and a beamforming parameter.

6. The method of claim 1 wherein (b) comprises initiating optimization in response to input from a user.

7. The method of claim 1 wherein (b) comprises initiating optimization after an amount of change corresponding to the first type of change is stable.

8. The method of claim 1 wherein (a) comprises identifying the first type of change after accounting for the second type of change.

9. A method for automatically altering medical image processing, the method comprising:
   (a) automatically identifying a type of change from frames of data for medical imaging; and
   (b) optimizing image processing in response to a first type of change differently than to a second type of change;
   wherein (a) comprises;
   (a1) comparing the frames of data with a reference frame of data;
   (a2) accounting for cyclical change in the comparison; and
   (a3) identifying change other than the cyclical change; and
   wherein (b) comprises initiating optimization in response to the change other than the cyclical change.

10. The method of claim 9 wherein (a2) comprises modeling a cyclical change as a function of the comparison of (a1).

11. The method of claim 9 wherein (a1) comprises calculating a change parameter as a function of time, (a2) comprises identifying peaks of the change parameter, times between successive peaks and magnitudes of the peaks, both (a1) and (a2) performed over a first time period and (a3) comprises comparing a current peak magnitude and time since a last peak with an expected peak magnitude and expected time since a last peak, the expected peak magnitude and expected time since a last peak determined as a function of (a1) and (a2).

12. A method for automatically altering medical image processing, the method comprising:
   (a) automatically identifying a type of change from frames of data for medical imaging; and
   (b) optimizing image processing in response to a first type of change differently than to a second type of change;
   wherein (a) comprises identifying change due to movement of the imaging plane relative to the patient and (b) comprises initiating adaptive calculation of gain in response to the movement of the imaging plane while avoiding the initiation in response to cyclical change due to a heart of the patient.

13. An ultrasound medical imaging method for initiating calculation of gain, the method comprising:
   (a) determining change due to repositioning of an imaging plane, the determining calculated from first ultrasound data;
   (b) accounting for change due to heart motion, breathing motion or both heart and breathing motion in the determination of (a);
   (c) setting a gain, a dynamic range or the gain and the dynamic range calculated from second ultrasound data; and
   (d) initiating (c) as a function of (a).

14. The method of claim 13 wherein (c) comprises setting a gain adaptively as a function of tissue signals of the second ultrasound data.

15. The method of claim 13 wherein (c) comprises setting a dynamic range adaptively as a function of noise signals of the second ultrasound data.

16. The method of claim 13 wherein (a) comprises determining the change from a set of frames of data and (c) comprises setting calculated from at least one of the frames of data from the set of frames of data.

17. The method of claim 13 wherein (c) comprises selecting a mapping function adaptively as a function of the second ultrasound data.

18. The method of claim 13 wherein (a) comprises determining the change in position of the imaging plane and subsequent lack of change in the position of the imaging plane and (d) comprises initiating (c) after determining the change in position and the subsequent lack of change in the position of the imaging plane.

19. The method of claim 13 wherein (b) comprises:
   (b1) comparing a plurality of frames of ultrasound data with a reference frame of data;
   (b2) accounting for cyclical change in the comparison; and
   (b3) identifying motion other than the cyclical motion;
   wherein (d) comprises initiating setting in response to the motion other then the cyclical motion.

20. A system for automatically altering medical image processing, the system comprising:
   a control processor for automatically identifying a type of change from frames of data for medical imaging and for initiating optimization of image processing in response to a first type of change differently than to a second type of change; and
   an image processing processor responsive to an initiation from the control processor to begin optimization of image processing;
   wherein the first type of change is at least one of transducer motion and in imaging plane differences, the control processor operable to avoiding initiation of optimization in response to the second type of change being at least one of heart and breathing cycle changes.

* * * * *